(12) United States Patent
Grattan

(10) Patent No.: US 7,993,673 B2
(45) Date of Patent: Aug. 9, 2011

(54) SWALLOW TABLET COMPRISING PARACETAMOL

(75) Inventor: Timothy James Grattan, Weybridge (GB)

(73) Assignee: SmithKline Beecham Limited, Brentford, Middlesex (GB)

( * ) Notice: Subject to any disclaimer, the term of this patent is extended or adjusted under 35 U.S.C. 154(b) by 0 days.

(21) Appl. No.: 10/480,960

(22) PCT Filed: Jun. 3, 2002

(86) PCT No.: PCT/EP02/06046
§ 371 (c)(1),
(2), (4) Date: Dec. 3, 2003

(87) PCT Pub. No.: WO02/100391
PCT Pub. Date: Dec. 19, 2002

(65) Prior Publication Data
US 2004/0170681 A1    Sep. 2, 2004

(30) Foreign Application Priority Data
Jun. 8, 2001 (GB) .................................. 0114069.8

(51) Int. Cl.
*A61K 9/20* (2006.01)
(52) U.S. Cl. ........ 424/464; 424/472; 424/484; 424/488; 424/465; 424/468
(58) Field of Classification Search .................... 424/489
See application file for complete search history.

(56) References Cited

U.S. PATENT DOCUMENTS

| 3,390,049 | A | * | 6/1968 | Reduick et al. ............... 424/481 |
| 4,405,800 | A |   | 9/1983 | Margetts et al. ............... 549/419 |
| 4,915,953 | A |   | 4/1990 | Jordan et al. ................. 424/473 |
| 5,073,377 | A |   | 12/1991 | Alexander et al. ............ 424/458 |
| 5,262,179 | A | * | 11/1993 | Gregory et al. ............... 424/489 |
| 5,424,075 | A |   | 6/1995 | Daher et al. .................. 424/465 |
| 5,750,145 | A | * | 5/1998 | Patell .......................... 424/478 |
| 6,149,938 | A | * | 11/2000 | Bonadeo et al. .............. 424/464 |
| 6,277,409 | B1 | * | 8/2001 | Luber et al. ................... 424/476 |
| 6,284,274 | B1 |  | 9/2001 | Merrill et al. ................. 424/472 |
| 6,316,025 | B1 | * | 11/2001 | Grattan ........................ 424/451 |
| 6,372,255 | B1 |  | 4/2002 | Saslawski et al. ............ 424/473 |
| 6,602,520 | B1 |  | 8/2003 | Schroeder et al. ........... 424/466 |

FOREIGN PATENT DOCUMENTS

| AU | 199741871 | 10/1997 |
| EP | 0418564 A | 3/1991 |
| EP | 0737473 A | 10/1996 |
| GB | 2103087 A | 2/1893 |
| WO | WO 98/38983 | 9/1998 |
| WO | WO98 46215 | 10/1998 |
| WO | WO99 04758 | 2/1999 |
| WO | WO 02/36101 | 5/2002 |

OTHER PUBLICATIONS

Stillings, et al., Current Medical Research and Opinion, vol. 16(2) pp. 115-124 (2000).
Rygnestad, et al., Eur J Clin Pharmacology, vol. 56 pp. 141-143 (2000).
Moeller, et al., J Clin Pharmacology, vol. 40 pp. 370-378 (2000).
Grattan, et al., Eur J Pharm Biopharm, vol. 43(3) pp. 225-229 (2000).

* cited by examiner

*Primary Examiner* — Robert A Wax
*Assistant Examiner* — Hasan Ahmed
(74) *Attorney, Agent, or Firm* — Dara L. Dinner; Theodore R. Furman

(57) ABSTRACT

A dosage form such as a swallow tablet or a capsule formulation is described comprising paracetamol, low levels of sodium bicarbonate or potassium bicarbonate or mixtures thereof, and at least one pharmaceutically acceptable excipient.

34 Claims, 1 Drawing Sheet

SWALLOW TABLET COMPRISING PARACETAMOL

BACKGROUND OF THE INVENTION

The present invention relates to pharmaceutical compositions containing N-acetyl-p-aminophenol, known by the generic names paracetamol, acetaminophen and APAP (hereinafter referred to as paracetamol). In particular, the invention relates to a fast acting paracetamol formulation containing a small amount of antacid, the formulation being in the form of a swallow tablet or capsule or other like dosage form.

Paracetamol is a commonly used analgesic and antipyretic drug that has been available in many countries for more than 40 years. A wealth of experience clearly establishes it as the standard antipyretic and analgesic for mild to moderate pain states. However it is known that following ingestion of paracetamol in solid form, e.g. as a tablet or capsule, rate of drug absorption, and hence onset of pharmacological activity, may vary from patient to patient. Recently it has been reported that absorption of paracetamol in tablet form is greatly affected by food and that maximum plasma concentrations of paracetamol are not always reached, which could have implications for pain relief in some patients (Stillings M. et al, Current Medical Research and Opinion 16(2):115-124, 2000).

In the past, attempts have been made to improve paracetamol absorption, for example by the use of soluble paracetamol tablets. Such tablets have been shown to have a faster rate of absorption (Rygnestad T et al., Eur J Clin Pharmacol 56: 141-143, 2000) and a faster onset of analgesic action compared to conventional paracetamol tablets (Moeller P L. et al., J Clin Pharmacol. 40: 370-378, 2000). However soluble tablets are not always convenient as they have to be dissolved in water prior to administration and moreover paracetamol-containing solutions may be unpalatable to some patients.

According to United Kingdom patent publication GB 2 103 087 (Bristol-Myers), an improved rate of absorption is achieved by co-administering a therapeutic dose comprising from about 150 mg to about 2000 mg of paracetamol with from about 60 mg to about 1200 mg of an antacid. A preferred range of antacid is disclosed as being from about 400 mg to about 1000 mg with a so-called optimum range being from about 450 mg to 880 mg. GB 2 103 087 reports that when the various formulations exemplified therein were administered to healthy volunteers in the fasted state, it was found that the actual increase in rate of absorption was between 7 and 31% compared to conventional paracetamol tablets.

WO 98/38983 (SmithKline Beecham) reports that a tablet or capsule formulation containing a combination of sodium bicarbonate and paracetamol, wherein the paracetamol is present in an amount of at least 300 mg and the weight ratio of bicarbonate to paracetamol is at least 0.74 to 1, gives a statistically significant improvement in the rate of absorption over that obtained from a commercially available paracetamol tablet containing no sodium bicarbonate.

According to Grattan et al, (Grattan T. et al, Eur J Pharm Biopharm. 43(3): 225-229, 2000) compositions comprising 400 mg or 630 mg sodium bicarbonate increase the rate of absorption of paracetamol relative to conventional paracetamol tablets in fasted healthy volunteers. The authors suggest that the effect of sodium bicarbonate on paracetamol absorption may be dose dependent.

WO02/36101 (Laboratorios Belmac S.A.) discloses a galenic formulation comprising a basic mixture of paracetamol and citric acid, a weak alkali such as sodium bicarbonate/ sodium carbonate, sodium citrate on its own or mixed with other salts of weak organic acids and a pharmaceutically acceptable carrier. It is intended in WO02/36101 to provide a formulation that is both dispersible and soluble in water. The alkali is included for the purpose of increasing pH, which would otherwise be too low for use in highly dispersible soluble tablets. There is no disclosure or teaching of how to improve paracetamol absorption following ingestion of a paracetamol-containing solid dosage form designed to be swallowed.

DETAILED DESCRIPTION OF THE INVENTION

Figure 1:
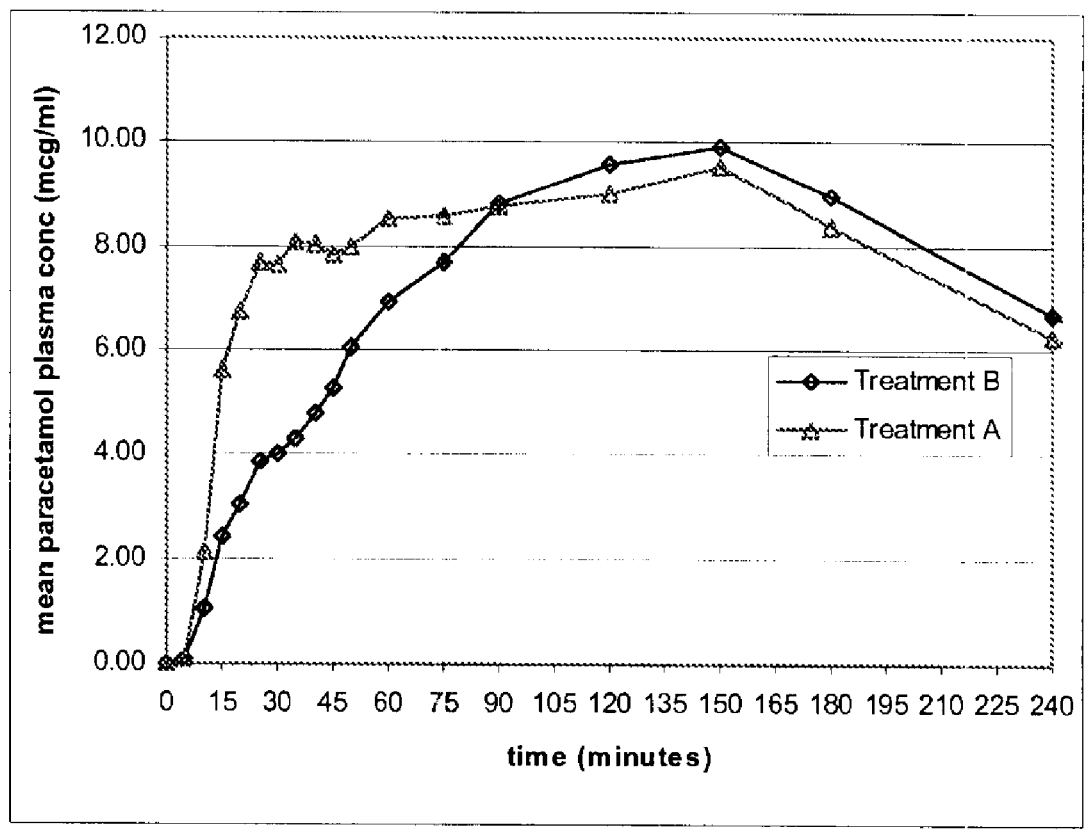
FIG. 1 demonstrates the mean plasma concentration vs. time for the first 4 hours following dosing, for Example 13.

The prior art referred to herein, other than WO02/36101, relate to paracetamol formulations having increased rates of absorption following ingestion of paracetamol in a solid form, such as a tablet or a capsule. Nevertheless there remains a need for alternative formulations; in particular because the approaches described in the prior art necessitate the use of large amounts of antacids which result in the formation of large tablets or capsules that may be difficult to swallow, at least for some patients. In addition use of a large amount of antacid(s) precludes the use of a high unit dose of paracetamol on account of the unacceptably large size of the resulting dosage form. Furthermore many of the antacids, at the levels used in the prior art, are not appropriate for use by all analgesic users; for example some users will be on sodium or potassium restricted diets, thus paracetamol tablets containing large amounts of sodium or potassium may pose a health risk for some individuals. It is desired to provide a paracetamol oral dosage form that is universally safe for all patients. In addition a paracetamol oral dosage form should combine the convenience of a conventional swallow tablet or capsule, including being small enough to be easily swallowed, and should be rapidly absorbed, irrespective of the dietary state of the patient, which as mentioned above may influence plasma concentrations of the drug. It is also desired to provide a fast acting, high unit dose (in the order of 1 g/unit dose) paracetamol formulation suitable for direct administration. It is an object of the present invention to provide a dosage form to meet these requirements.

According to the present invention there is provided a dosage form intended to be swallowed directly such as a swallow tablet or capsule formulation comprising a therapeutically effective amount of paracetamol, a pharmaceutically acceptable excipient and an amount of antacid up to 100 mg per unit dose wherein the antacid is sodium bicarbonate or potassium bicarbonate or mixtures thereof.

For the avoidance of doubt, a dosage form according to the invention is one that is intended to be swallowed in solid form, and includes, but is not limited to swallow tablets, pills, capsules and caplets. Suitably the dosage form of the invention is a non-effervescent dosage form. A dosage form intended for dispersion in the mouth or intended for dissolution or suspension in water prior to administration, e.g. a dosage form containing a substantial amount of an effervescent couple or a dosage form containing an edible acid, e.g. citric acid or tartaric acid, in an amount sufficient to produce effervescence on reaction with an antacid on exposure to water, is not encompassed within the scope of the invention. Such a dosage form requires protection from moisture during handling and storage, which is not a requirement of a dosage form according to the invention.

The present invention is based on the unexpected finding that a small amount of a specific antacid or antacids, namely sodium bicarbonate, potassium bicarbonate or mixtures thereof, enhance the dissolution rate of paracetamol, compared to corresponding formulations containing no sodium bicarbonate and/or potassium bicarbonate. The significance of this finding is that an enhanced dissolution rate is known in the art to be predictive of improved absorption in vivo. It has been found that dissolution rate is not enhanced, or at least not to the same extent as that observed with the antacid(s) of the invention, when other antacids, namely sodium carbonate, potassium carbonate, calcium carbonate, magnesium hydroxide and magnesium carbonate are combined with paracetamol in a solid dosage form at equivalent levels. More surprisingly, the dissolution rate is not enhanced to the same extent as that observed with the antacid(s) of the invention, when paracetamol is combined with the superdisintegrant, croscarmallose sodium, at equivalent levels. Accordingly inclusion of an antacid, other than an antacid of the invention, such as sodium carbonate, potassium carbonate, calcium carbonate, magnesium hydroxide or magnesium carbonate and mixtures thereof, and/or a superdisintegrant, such as croscarmallose sodium, in a dosage form of the invention is entirely optional.

Suitably dissolution rate may be determined by a dissolution method that utilizes a USP Paddle apparatus, employing 900 ml of 0.05M HCl and a stirrer speed of 30 rpm. It has been found that this dissolution method, unlike the USP method described in the USP Monograph for paracetamol tablets, has been especially effective in discriminating between different paracetamol formulations. Moreover it is also believed that the dissolution method employed herein more accurately reflects the hydrodynamic conditions encountered in the stomach mileau, and especially reflects the dissolution process following ingestion of a paracetamol formulation in the stomach, particularly in a fed state. Suitably the dissolution rate of an uncoated dosage form of the invention, e.g. a tablet without a film-coating, as determined by the dissolution method described herein, is such that at least 78% of the paracetamol is released within 15 minutes, preferably at least 85% paracetamol is released within 15 minutes, and even more preferably at least 90% or more paracetamol is released within 15 minutes. Dissolution of paracetamol from a coated dosage form of the invention e.g. a film-coated, sugar-coated or gelatine-coated tablet, may have a longer release time e.g. up to five minutes longer compared to an equivalent uncoated dosage form. However notwithstanding this, the dissolution rate of a coated dosage form of the invention is significantly improved compared to the dissolution rate of commercially available paracetamol tablets. Typically the dissolution rate of a film-coated dosage form of the invention is such that at least 85% of the paracetamol is released within 20 minutes, preferably at least 90% is released within 20 minutes.

By "therapeutically effective amount of paracetamol" is meant an amount of paracetamol sufficient to achieve a therapeutic benefit. Suitably such an amount is in the range 250 mg to 1000 mg per unit dose e.g. 250 mg to 600 mg per unit dose and typically is 325 mg, 500 mg, or 1000 mg paracetamol per unit dose. By "per unit dose" is meant per tablet, capsule or other dosage unit.

The amount of antacid in a dosage form of the invention should be sufficient to ensure that using the dissolution method employed herein, at least 78% of the paracetamol in the dosage form i.e. at least in an uncoated dosage form, has been released within 15 minutes. Suitably the amount of antacid per unit dose is an amount up to 100 mg, preferably in the range 2 to 100 mg or 2 to 90 mg, more preferably 2 to 75 mg or 3 to 55 mg, even more preferably 4 to 30 mg and most preferably 5 to 15 mg. Typically when paracetamol is present in an amount ranging from 250 mg to 600 mg per unit dose, the amount of sodium bicarbonate or potassium bicarbonate is in the range 4 to 30 mg, preferably 5 to 15 mg or 10 to 15 mg per unit dose. Typically when paracetamol is present in an amount greater than 600 mg e.g. in the range 600-1000 mg, the amount of sodium bicarbonate or potassium bicarbonate is in the range 8 to 60 mg, preferably 10 to 30 mg or 20 to 30 mg per unit dose. Advantageously the use of relatively low amounts of the antacid component enables the provision fast-acting dosage forms that are small or smaller in size than have been possible hitherto.

In another aspect, a dosage form of the invention comprises a combination or mixture of the antacids, sodium bicarbonate and potassium bicarbonate. When a combination or mixture of the antacids is used, the total amount of antacid should not exceed 100 mg per unit dose. Preferably each antacid is present in an amount ranging from 2 to 100 mg or 2 to 90 mg, more preferably 2 to 75 mg or 3 to 55 mg, even more preferably 4 to 30 mg and most preferably 5 to 15 mg. Typically when paracetamol is present in an amount ranging from 250 mg to 600 mg per unit dose, the amount of each antacid is in the range 4 to 30 mg, preferably 5 to 15 mg or 10 to 15 mg per unit dose. Suitably the total amount of antacid per unit dose is in the range 10 to 30 mg, preferably 10 to 25 mg. Typically when paracetamol is present in an amount greater than 600 mg e.g. in the range 600-1000 mg, the amount of each antacid is in the range 8 to 60 mg, preferably 10 to 30 mg or 20 to 30 mg per unit dose. Suitably the total amount of antacid per unit dose is in the range 20 to 60 mg, preferably 20 to 50 mg.

Formulations of the invention will generally contain at least one pharmaceutically acceptable excipient conventionally used in the art of solid dosage form formulation. Suitable excipients which may be incorporated include lubricants, for example magnesium stearate and stearic acid; disintegrants, for example cellulose derivatives; starches; binders, for example modified starches and cellulose derivatives; glidants, for example colloidol silicas; compression aids, for example cellulose derivatives; as well as preservatives, suspending agents, wetting agents, flavouring agents, bulking agents, adhesives, colouring agents, sweetening agents appropriate to their form. Suitably when the composition is in a tablet form, the composition will further comprise a film coat e.g. HPMC. Suitably the film coat is a transparent film coat, although an opaque film coat e.g. as obtained when using a film coat material in combination with an opacifier or a pigment such as titanium dioxide, a lake or a dye, may also be used. Advantageously it has been found that the inclusion of an opaque film coat minimizes tablet discoloration, which may occur on long-term storage of the tablet. Discoloration may also be avoided by incorporating a colouring agent into the tablet core. Suitably such tablets may also be film-coated, e.g. if desired for aesthetic purposes and/or to aid swallowing.

In addition to paracetamol, an antacid as described herein, and a pharmaceutically acceptable excipient, dosage forms of the invention may also contain other pharmaceutically active agents, for example other analgesics, anti-inflammatory analgesic agents, decongestants, diuretics e.g. pamabrom, non-sedating and sedating antihistamines e.g. diphenydramine, doxylamine and mepyramine, gastrointestinal agents e.g. metoclopramide, muscle relaxants e.g. methocarbamol, antitussive agents, etc. Formulations may also contain a pharmaceutically acceptable analgesic adjuvant, for example caffeine.

The invention also provides a process for the preparation of a dosage form e.g. tablet or capsule formulation of the invention, which process comprises the admixture of paracetamol sodium bicarbonate or potassium bicarbonate or mixtures thereof (hereinafter referred to as the 'bicarbonate(s)'), together with any pharmaceutically acceptable excipients, additional pharmaceutically acceptable active agents or adjuvants. Thus the paracetamol and the bicarbonate(s) may be mixed together with one or more binders and granulated using water. The resulting granule may then be dried, sieved and mixed with additional excipients such as a lubricant and disintegrant before being compressed into tablets. Alternatively, the bicarbonate(s) may be omitted from the granulation step and subsequently added with the other excipients.

In an alternative process, tablets may be prepared using direct compression grades of paracetamol including commercially available forms which obviates the need for a granulation step. Tablets may also be prepared by other processes known in the art such as by shaping of an extruded mixture. For capsule production, the paracetamol and the bicarbonate(s) may be mixed and granulated as for tablet production and filled into suitably sized capsule shells to the desired fill weight.

Examples 1 to 5, 8 and 11 to 14 are illustrations of the invention. Comparative Examples 6, 7, 9 and 10 are outside the scope of the invention but are included to further demonstrate the advantages of the invention.

Example 1

Tablets were prepared with the following composition:

|   | Ingredient | Mg/tablet |
|---|---|---|
| 1 | Paracetamol BP/Ph. Eur. Fine | 500.00 |
| 2 | Starch, Maize Ph. Eur. | 11.40 |
| 3 | Starch, Pregelatinized NF. | 50.00 |
| 4 | Povidone Ph. Eur. K25 | 2.00 |
| 5 | Potassium Sorbate BP/Ph. Eur. | 0.60 |
| 6 | Starch Maize Ph Eur | 10.00 |
| 7 | Stearic acid | 5.00 |
| 8 | Talc | 15.00 |
| 9 | Sodium bicarbonate | 50.00 |

1. Items 1-5 were granulated with water, dried and then sieved to produce a fine white granule.
2. Item 6 was blended with the granule from step 1 followed by items 7 and 8.
3. Item 9 was mixed with the blend from step 2.
4. The blend from step 3 was compressed using a suitable tablet press to give white caplets containing Paracetamol 500 mg, sodium bicarbonate 50 mg with a target hardness of 7 kp (10 scu).

Example 2

Tablets were prepared with the following composition:

|   | Ingredient | Mg/tablet |
|---|---|---|
| 1 | Paracetamol BP/Ph. Eur. Fine | 500.00 |
| 2 | Starch, Maize Ph. Eur. | 11.40 |
| 3 | Starch, Pregelatinized NF. | 50.00 |
| 4 | Povidone Ph. Eur. K25 | 2.00 |
| 5 | Potassium Sorbate BP/Ph. Eur. | 0.60 |
| 6 | Avicel PH105 Ph. Eur | 89.00 |
| 7 | Magnesium Stearate Ph. Eur | 6.00 |
| 8 | Potassium bicarbonate | 12.00 |
| 9 | Sodium bicarbonate | 10.00 |

1. Items 1-5 were granulated with water, dried and then sieved to produce a fine white granule.
2. Item 6 was blended with the granule from step 1 followed by blending with item 7.
3. Items 8 and 9 were mixed with the blend from step 2.
4. The blend from step 3 was compressed using a suitable tablet press to give white caplets containing Paracetamol 500 mg, sodium bicarbonate 10 mg and potassium bicarbonate 12 mg with a target hardness of 7 kp (10 scu).

Example 3

Further batches of tablets were prepared as outlined in Example 1, but sodium bicarbonate 50 mg/tablet was replaced with the ingredients as listed below:

| Example | Ingredient | mg/tablet |
|---|---|---|
| 3A | Sodium Bicarbonate | 10 |
| 3B | Sodium Bicarbonate | 5 |
| 3C | Potassium Bicarbonate | 10 |
| 3D | Potassium Bicarbonate | 5 |
| 3E | Sodium bicarbonate | 2 |
| 3F | Potassium Bicarbonate | 50 |
| 3G | Potassium Bicarbonate | 12 |

Example 4

Tablets with a transparent film coat may be prepared with the following composition:

|   | Ingredient | mg/tablet |
|---|---|---|
| 1 | Tablets from example 1 | 644.00 |
| 2 | Hydroxypropylmethyl cellulose | 4.17 |
| 3 | Triacetin | 0.73 |

Sufficient materials should be weighed out to produce approximately 5 Kg of tablets. Mix items 2 and 3 in a suitable volume of water until a homogenous mix is obtained. Spray the mixture onto item 1 in a suitable coating pan to yield white film coated tablets containing paracetamol 500 mg/tablet and sodium bicarbonate 50 mg per tablet.

Example 5

Tablets with an opaque film coat may be prepared with the following composition:

|   | Ingredient | mg/tablet |
|---|---|---|
| 1 | Tablets from example 1 | 644.00 |
| 2 | Hydroxypropylmethyl cellulose | 4.17 |
| 3 | Triacetin | 0.73 |
| 4 | Titanium dioxide powder | 0.10 |

Sufficient materials should be weighed out to produce approximately 5 Kg of tablets. Mix items 2 and 3 in a suitable volume of water until a homogenous mix is obtained and suspend item 4 in the resulting solution. Spray the mixture onto item 1 in a suitable coating pan to yield white film coated tablets containing paracetamol 500 mg/tablet and sodium bicarbonate 50 mg per tablet.

Example 6

Further batches of tablets were prepared as outlined in Example 1, but sodium bicarbonate 50 mg/tablet was replaced with the ingredients as listed below:

| Example # | Ingredient | mg/tablet |
|---|---|---|
| 6A | Sodium Carbonate | 50 |
| 6B | Potassium carbonate | 50 |
| 6C | Calcium Carbonate | 50 |
| 6D | Magnesium Hydroxide | 50 |
| 6E | Magnesium Carbonate | 50 |
| 6F | Crosscarmellose Sodium | 50 |

Example 7

Further batches of tablets were prepared as outlined in example 2, but the potassium bicarbonate and sodium bicarbonate 10 mg/tablet was replaced with the ingredients as listed below:

| Example # | Ingredient | mg/tablet |
|---|---|---|
| 7A | No additive | — |
| 7B | Sodium sesquicarbonate | 50 |

Example 8

Dissolution Studies

Dissolution studies were conducted on tablets from Examples 1, 2 and 3 using the USP paddle apparatus with 1 litre of 0.05M HCl and a paddle speed of 30 rpm. The amount of paracetamol dissolved after 15 minutes is shown in TABLE 1:

TABLE 1

| Example | Ingredient | mg/tablet | % dissolved at 15 minutes |
|---|---|---|---|
| 1 | Sodium bicarbonate | 50 | 98.5 |
| 2 | Potassium bicarbonate | 12 | 98.0 |
|   | Sodium Bicarbonate | 10 | 98.3 |
| 3A | Sodium bicarbonate | 10 | 98.0 |
| 3B | Sodium Bicarbonate | 5 | 81.2 |
| 3C | Potassium Bicarbonate | 10 | 97.9 |
| 3D | Potassium Bicarbonate | 5 | 95.4 |
| 3E | Sodium bicarbonate | 2 | 78.5 |
| 3F | Potassium Bicarbonate | 50 | 99.2 |
| 3G | Potassium Bicarbonate | 12 | 98.1 |

Example 9

Further dissolution studies were conducted on tablets from Examples 6 and 7 using the USP paddle apparatus with 900 ml of 0.05M HCl and a paddle speed of 30 rpm. The amount of paracetamol dissolved after 15 minutes is shown in TABLE 2:

TABLE 2

| Example # | Ingredient | mg/tablet | % dissolved at 15 minutes |
|---|---|---|---|
| 6A | Sodium Carbonate | 50 | 45.9 |
| 6B | Potassium carbonate | 50 | 74.7 |
| 6C | Calcium Carbonate | 50 | 40.3 |
| 6D | Magnesium Hydroxide | 50 | 34.0 |

TABLE 2-continued

| Example # | Ingredient | mg/tablet | % dissolved at 15 minutes |
|---|---|---|---|
| 6E | Magnesium Carbonate | 50 | 33.7 |
| 6F | Crosscarmellose Sodium | 50 | 76.7 |
| 7A | No additive | — | 43.2 |
| 7B | Sodium sesquicarbonate | 50 | 71.8 |

Example 10

Further dissolution studies were conducted on various different commercially available paracetamol tablets using the USP paddle apparatus with 1 litre of 0.05M HCl and a paddle speed of 30 rpm. The amount of paracetamol dissolved after 15 minutes is shown in TABLE 3:

TABLE 3

| Commercial product | % dissolved at 15 minutes |
|---|---|
| A | 43.7 |
| B | 38.1 |
| C | 40.5 |
| D | 61.0 |
| E | 31.5 |
| F | 63.8 |
| G | 64.1 |
| H | 27.3 |
| I | 50.3 |
| J | 45.2 |
| K | 47.4 |
| L | 64.0 |
| M | 44.6 |
| N | 28.7 |
| O | 31.1 |
| P | 57.3 |

The results indicated that the commercial products gave significantly lower dissolution rates compared to those of the dosage forms of the invention.

Example 11

Batches of tablets were prepared with the following compositions:

| | Ingredients | Batch A Mg/tablet | Batch B Mg/tablet |
|---|---|---|---|
| 1 | Paracetamol BP/Ph. Eur. Fine | 500.00 | 500.00 |
| 2 | Starch, Pregelatinized NF. | 75.00 | 75.00 |
| 3 | Povidone Ph. Eur K25 | 2.50 | 2.50 |
| 4 | Potassium Sorbate BP/Ph. Eur. | 0.60 | 0.60 |
| 5 | Crospovidone (Kollidon CL) | 5.70 | 5.70 |
| 6 | Sodium Bicarbonate | 75.00 | 100.00 |
| 7 | Magnesium Stearate | 3.00 | 3.00 |

Dissolution studies were conducted as described in Example 8. The amount of paracetamol dissolved after 15 minutes was 94.7% for Batch A and 94.5% for Batch B.

Example 12

Tablets were prepared as outlined in Example 2 with the following composition:

|   | Ingredient | mg/tablet |
|---|---|---|
| 1 | Paracetamol BP/Ph. Eur. Fine | 500.00 |
| 2 | Starch, Maize Ph. Eur. | 11.40 |
| 3 | Starch, Pregelatinized NF. | 50.00 |
| 4 | Povidone Ph. Eur. K25 | 2.00 |
| 5 | Potassium Sorbate BP/Ph. Eur. | 0.60 |
| 6 | Avicel PH105 Ph. Eur | 89.00 |
| 7 | Magnesium Stearate Ph. Eur | 6.00 |
| 8 | Potassium bicarbonate | 11.5 |
| 9 | Sodium bicarbonate | 10.00 |

Dissolution studies were conducted as described in Example 8. The amount of paracetamol dissolved after 15 minutes was >99%.

Example 13

Biostudy

This was a single center, open, single dose, four-way crossover human pharmacology (Phase I) study. A total of 28 eligible subjects were recruited to ensure that 24 evaluable subjects completed the study. There were four study sessions comprising of twelve hours of blood sampling post-dose. There was a wash-out period of at least three days from the time of dosing between study sessions. During each study session subjects undertook one of the four regimens (arms) under test according to a randomization schedule.

One of the test treatments (treatment A) comprised of 2 tablets from example 11 and another of the test treatments (treatment B) comprised of 2 commercially available paracetamol 500 mg tablets which do not contain sodium or potassium bicarbonate.

At the beginning of each study session subjects received one of the study formulations (2 tablets) at a time interval approximately between 8:00 am and 9:00 am. For all 4 study sessions the volunteers fasted overnight, for treatments A and B the subjects consumed a cooked breakfast 30 minutes prior to dosing. Blood samples (3 ml) were taken within 15 minutes pre-dose and then at further specified times post-dose within twelve hours.

This study was conducted over approximately four weeks and included a pre-study screen, four study sessions (each approximately 20 hours duration) and three wash-out periods of at least three days duration.

Plasma samples were analysed for paracetamol using a validated HPLC-UV method.

Mean plasma concentration vs time plots for the first 4 hours following dosing are shown in FIG. 1 below.

Subsequent pharmacokinetic analysis (Table 4) indicated that the Area under the plasma concentration vs time profiles for the first 20 minutes ($AUC_{0-20}$), 60 minutes ($AUC_{0-60}$) and 90 minutes ($AUC_{0-90}$) following dosing were significantly greater for Treatment A compared to treatment B. Furthermore, the median time to achieve the putative minimum therapeutic plasma concentration (4 mcg/ml) was significantly faster for treatment A (25 minutes) compared to treatment B (45.5 minutes) indicating that pain relief should be achieved approximately 20 minutes more quickly for treatment A compared to treatment B.

TABLE 4

Comparison of pharmacokinetic parameters for treatment A and treatment B

|   | $AUC_{0-20}$ (µg · min/ml) | $AUC_{0-60}$ (µg · min/ml) | $AUC_{0-90}$ (µg · min/ml) |
|---|---|---|---|
| Treatment A | 17* | 300* | 559* |
| Treatment B | 5* | 155* | 352* |
| Median difference | 9 | 70 | 85 |
| 90% CI** | [5, 53] | [45.5, 241] | [37, 276] |
| 95% CI** | [3.5, 57] | [31.5, 256] | [17, 294.5] |
| P value | 0.0030 | 0.0027 | 0.0088 |

\* = median
\*\* = [lower, upper] for median difference

Example 14

Uncoated tablets from Example 12 were sprayed with an aqueous solution containing titanium dioxide, polydextrose, BPMC, triacetin and polyethylene glycol to produce white film coated tablets with approximately 2.5% w/w film coat. The tablets were tested using the method described in Example 8. The amount of paracetamol dissolved after 15 minutes was 88.2%. After 20 minutes the amount of paracetamol dissolved was 90.9%.

The invention claimed is:

1. A non-effervescent dosage form comprising a pharmaceutical composition comprising a therapeutically effective amount of paracetamol, and an antacid consisting essentially of sodium bicarbonate or potassium bicarbonate or mixtures thereof present in an amount from 3 mg to 55 mg together with any pharmaceutically acceptable excipients, additional pharmaceutically acceptable active agents or adjuvants, to provide release of at least 78% of the paracetamol is released with 15 minutes as determined by a dissolution method that utilizes a USP paddle, employing 900 ml of 0.05M HCl and a stirrer speed of 30 rpm; and wherein the dosage form is a non-effervescent uncoated swallow tablet or capsule.

2. The dosage form according to claim 1 wherein amount of paracetamol is 325 mg.

3. The dosage form according to claim 1 wherein the amount of paracetamol is 500 mg.

4. The dosage form according to claim 1 wherein the amount of paracetamol is 1000 mg.

5. A non-effervescent pharmaceutical dosage form comprising a therapeutically effective amount of paracetamol and from 3 mg to 55 mg of antacid selected from the group consisting of sodium bicarbonate, potassium bicarbonate, and mixtures thereof sufficient to provide release of at least 85% of the paracetamol within 20 minutes as determined by a dissolution method that utilizes a USP paddle, employing 900 ml of 0.05M HCl and a stirrer speed of 30 rpm; and wherein the dosage form is a non-effervescent coated swallow tablet.

6. The dosage form according to claim 5 wherein the antacid is potassium bicarbonate in an amount in the range 4 to 30 mg.

7. The dosage form according to claim 5 wherein antacid is a combination of sodium and potassium bicarbonate and wherein each bicarbonate is in an amount in the range 4 to 30 mg.

8. The dosage form according to claim 5 wherein at least 90% of the paracetamol is released within 15 minutes.

9. The dosage form according to claim 1 further comprising a pharmaceutically active agent and/or a pharmaceutically acceptable analgesic adjuvant.

10. The dosage form according to claim 5 wherein the paracetamol is present in an amount of 250 mg to 1000 mg.

11. The dosage form according to claim 6 wherein the antacid is sodium bicarbonate in an amount in the range 4 to 30 mg.

12. The dosage form according to claim 1 wherein the antacid is present in an amount from 5 to 15 mg.

13. The dosage form according to claim 1 wherein the paracetamol is present in an amount from 250 to 600 mg.

14. The dosage form according to claim 1 wherein the paracetamol is present in an amount from greater 600 mg to 1000 mg and the antacid is present in an amount from 20 to 50 mg.

15. The dosage form according to claim 5 wherein the antacid is present in an amount from 5 to 15 mg.

16. The dosage form according to claim 5 wherein the antacid is present in an amount from 4 to 30 mg.

17. The dosage form according to claim 5 wherein the paracetamol is present in an amount from 250 to 600 mg.

18. The dosage form according to claim 5 wherein the paracetamol is present in an amount from greater than 600 mg to 1000 mg and the antacid is present in an amount from 20 to 50 mg.

19. The dosage form according to claim 1 wherein the antacid is present in an amount from 5 to 15 mg, and wherein the dosage form is a capsule.

20. The dosage form according to claim 1 wherein the antacid is presented in an amount from 4 to 30 mg, and wherein the dosage form is a capsule.

21. The dosage form according to claim 1 wherein the paracetamol is present in an amount from 250 to 600 mg.

22. The dosage form according to claim 1 wherein the paracetamol is present in an amount from greater than 600 mg to 1000 mg and the antacid is present in an amount from 20 to 50 mg.

23. The dosage form according to claim 5 wherein the coated tablet comprises an opaque film coat.

24. The dosage form according to claim 5 wherein the coated tablet comprises a transparent film coat.

25. The dosage form according to claim 5 wherein the amount of paracetamol is 325 mg.

26. The dosage form according to claim 5 wherein the amount of paracetamol is 500 mg.

27. The dosage form according to claim 5 wherein the amount of paracetamol is 1000 mg.

28. The dosage form according to claim 5 wherein the coated tablet comprises a sugar coating.

29. The dosage form according to claim 5 wherein the coated tablet comprises a gelatin coating.

30. The dosage form according to claim 23 wherein the opaque film coat is a film coating material in combination with an opacifier, a pigment, a lake or a dye.

31. The dosage form according to claim 5 further comprising a pharmaceutically active agent and/or a pharmaceutically acceptable analgesic adjuvant.

32. The dosage form according to claim 31 wherein the pharmaceutically acceptable analgesic adjuvant is caffeine.

33. The dosage form according to claim 16 wherein the antacid is sodium bicarbonate.

34. The dosage form according to claim 16 wherein the antacid is potassium bicarbonate.

* * * * *